(12) United States Patent
Carvani et al.

(10) Patent No.: US 9,770,264 B2
(45) Date of Patent: Sep. 26, 2017

(54) DEVICE FOR FIXING A CRANIAL LIMB TO THE CRANIAL CROWN TO BE PLACED IN THE CRANIOTOMIAL HOLE OR CUTTING, DEDICATED APPLYING DEVICE AND PROCESS FOR ITS USE

(75) Inventors: Moreno Carvani, Rival Scrivia (IT); Igino Romolo Gazzani, Rivalta Scrivia (IT); Piero Cavigliasso, Rivalta Scrivia (IT)

(73) Assignee: NT-PLAST S.R.L., Rivalta Scriva (AL) (IT)

( * ) Notice: Subject to any disclaimer, the term of this patent is extended or adjusted under 35 U.S.C. 154(b) by 617 days.

(21) Appl. No.: 14/384,846

(22) PCT Filed: Mar. 12, 2012

(86) PCT No.: PCT/IT2012/000068
§ 371 (c)(1),
(2), (4) Date: Sep. 12, 2014

(87) PCT Pub. No.: WO2013/136348
PCT Pub. Date: Sep. 19, 2013

(65) Prior Publication Data
US 2017/0189069 A1    Jul. 6, 2017

(51) Int. Cl.
*A61B 17/68* (2006.01)
*A61B 17/88* (2006.01)

(52) U.S. Cl.
CPC ........ *A61B 17/688* (2013.01); *A61B 17/8872* (2013.01)

(58) Field of Classification Search
CPC ..................... A61B 17/688; A61B 17/8872
See application file for complete search history.

(56) References Cited

U.S. PATENT DOCUMENTS 6,379,363 B1 *   4/2002  Herrington ......... A61B 17/688
                                                         606/104
2008/0281339 A1 * 11/2008 Kirschman ......... A61B 17/688
                                                         606/151

FOREIGN PATENT DOCUMENTS

DE              19952359 C1 *  3/2001  ........... A61B 17/688

* cited by examiner

*Primary Examiner* — Christian Sevilla
(74) *Attorney, Agent, or Firm* — Pasadena Legal Group; Norman R. Van Treeck

(57) ABSTRACT

A device is described, for fastening a cranial limb to the cranial crown adapted to be positioned both into a craniotomial hole and into a craniotomial cutting, comprising: a cortical supporting riser; first closing means operatively connected to the riser; second closing means to be fastened to the riser to complete its closing; and a handle connected to the cortical riser; wherein the first closing means are composed of at least two elastic arms operatively connected to the cortical riser and that end each one in at least one small transverse arm.

9 Claims, 6 Drawing Sheets

US 9,770,264 B2

DEVICE FOR FIXING A CRANIAL LIMB TO THE CRANIAL CROWN TO BE PLACED IN THE CRANIOTOMIAL HOLE OR CUTTING, DEDICATED APPLYING DEVICE AND PROCESS FOR ITS USE

CROSS-REFERENCE TO RELATED APPLICATION

The present Application is a national stage of International Patent Application No. PCT/IT2012/000068, titled "Device For Fixing a Cranial Limb To The Cranial Crown To Be Placed In The Craniotomial Hole Or Cutting, Dedicated Applying Device And Process For Its Use," filed Mar. 12, 2012, the contents of which are incorporated in this disclosure by reference in their entirety.

BACKGROUND OF THE INVENTION

The present invention refers to a device for fixing a cranial limb to the cranial crown to be placed in the craniotomial hole or cutting, to an applying device dedicated for such device and to the process for using such device.

The present invention is an improvement of the device disclosed in document WO-A1-2009/044421 of the same Applicant.

As known, craniotomy, namely incision and cutting a bone limb of the cranial crown, is the compulsory neuro-surgical procedure for treating any intra-cranial lesion.

The bone limb is cut by performing one or more drill holes, according to the procedure that provides for the use of a cutting blade or perforating device applied to the pneumatic drill, that, with free hand, from the key hole detach the dura mater below and simultaneously etches the bone.

At the end of the neuro-surgical intervention, after having sutured the dura mater and suspended the edges to the bone, the limb is laid again in the opening and fastened with separate metal or wire staples, made pass through small drill holes coupled on the free edge of the cranial bone.

It is however clear that this type of solution does not allow, in general, an aesthetically acceptable closure, since it is not always able to avoid that the bone limb can be projected, recessed, slanted or rotated.

SUMMARY OF THE INVENTION

Object of the present invention, therefore, is solving the above prior art problems, by providing a device for fixing a cranial limb to the cranial crown that allows a correct recovery and attachment of the bone limb to the edge of the cranial crown and simultaneously closes the holes obtained for the craniotomy.

Another object of the invention is providing a device that allows having a lower tension on the brain, even in case a brain edema occurs after the surgery.

With respect to the invention disclosed in the above mentioned patent WO-A1-2009/044421, that necessarily requires the presence of drill holes to be placed, the present invention can be inserted indifferently into the craniotomial hole or into the craniotomial cutting, thereby allowing to fix the limb in many points, even when a single hole has been drilled, or this latter one has an irregular shape. Moreover, the present invention includes an applying device dedicated to simplify the assembly of the device.

These and other objects are obtained by a device for fixing a cranial limb to the cranial crown to be placed into the craniotomial hole or into the craniotomial cutting as described in claim 1, and by an applying device and a process as described in their respective claims.

Further features of the invention are defined in the dependent claims.

It is intended that all claims are an integral part of the present document.

BRIEF DESCRIPTION OF THE DRAWINGS

Further objects and advantages of the present invention will be clear from the following description and from the attached drawings, provided merely as a non-limiting example, in which.

DETAILED DESCRIPTION OF PREFERRED EMBODIMENTS

Figure 1:
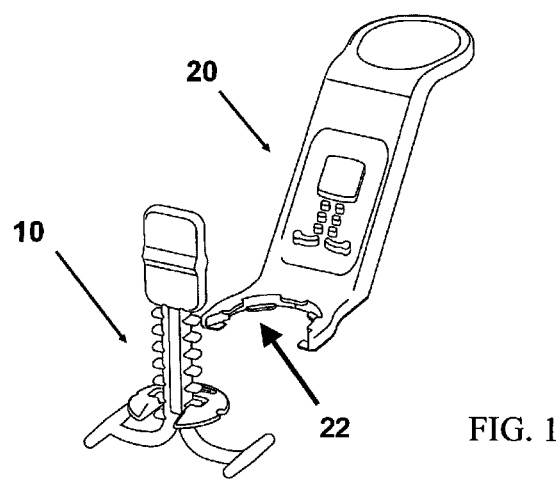
FIG. 1 shows a perspective view of a preferred embodiment of the device for fixing a cranial limb to the cranial crown to be placed into the craniotomial hole or the craniotomial cutting and a preferred embodiment of its dedicated applying device.
Figure 2A:
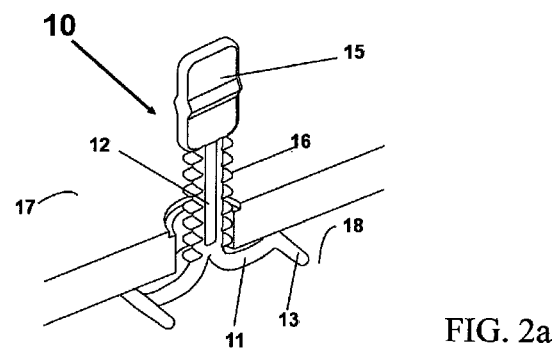
FIG. 2a is a view of the device of FIG. 1 in a first step of its use in the craniotomial hole.
Figure 2B:
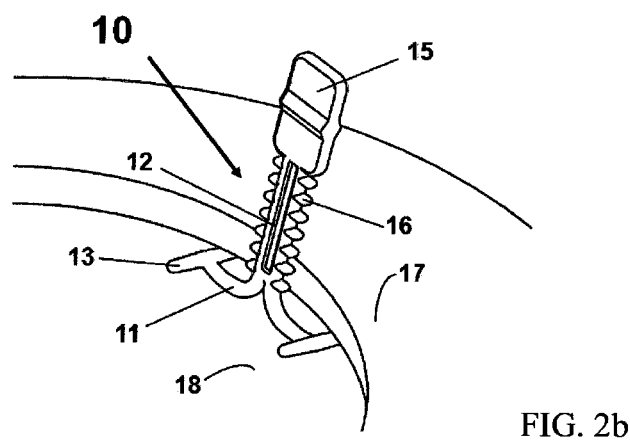
FIG. 2b is a view of the device of FIG. 1 in a first step of its use in the craniotomial cutting.

With particular reference to the cited Figures, the device for fixing a cranial limb to the cranial crown to be placed into the craniotomial hole or into the craniotomial cutting, according to the present invention, is globally designated by reference number 10.

The device 10 has elastic arms 11, joined to the cortical riser 12, and ending in small transverse arms 13, and an upper plate 14, (FIGS. 5a, 5b) that will have to be inserted into the upper part of, the cortical riser 12.

Figure 5A:
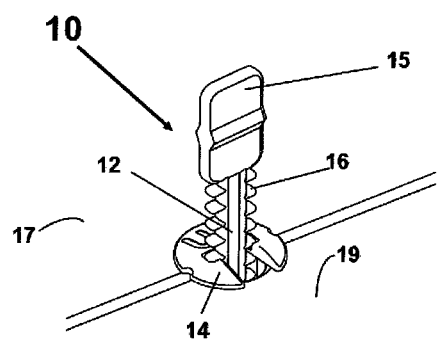
FIG. 5a shows a view of the device of FIG. 1 in a further step of its use in the craniotomial hole.
Figure 5B:
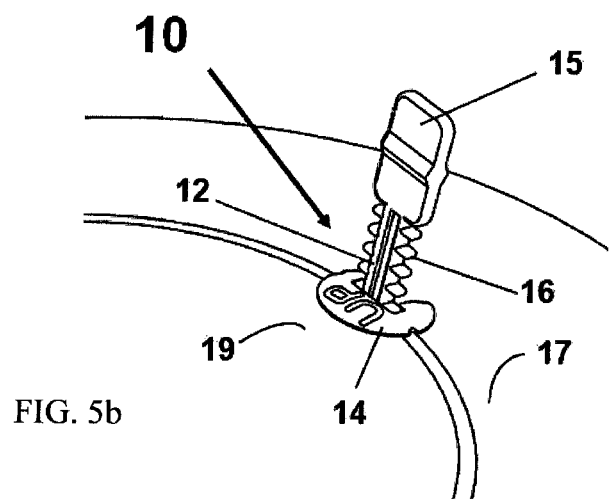
FIG. 5b shows a view of the device of FIG. 1 in a further step of its use in the craniotomial cutting.

The cortical riser 12 will be equipped with a handle 15 and a plurality of fastening elements 16 placed at as many levels along the length of the riser 12, fastening elements 16 that will be used for inserting the upper plate 14 (FIGS. 5a, 5b).

The cortical riser 12, that connects the elastic arms 11 and the upper plate 14, due to the elasticity of the arms 11, allows a fine adjustment to the bone thickness.

By examining in more detailed the application modes of the cranial fastening device 10 of the invention, it must be noted that the instrument operator prepares the right amount of devices 10 suitable for fixing the craniotomy.

Such operations are performed by choosing the more suitable number of devices 10, depending on the width and shape of the craniotomy.

The invention further deals with an applying device 20 adapted to operate with the above described device 10; such applying device 20 comprises a seat 22 adapted to support the upper plate 14 and to allow the operating coupling between such plate 14 and the cortical riser 12 when the craniotomial hole or the craniotomial cutting has been closed.

In order to position the device 10 into the craniotomial hole, the following operations are provided.

A surgeon inserts the device 10 into the craniotomial hole with the cortical riser 12 placed at the hole centre and perpendicular to the cranial surface, and so that part of the small cross arms 13 are placed in the space between the cranial crown 17 and the dura mater 18.

Figure 3A:
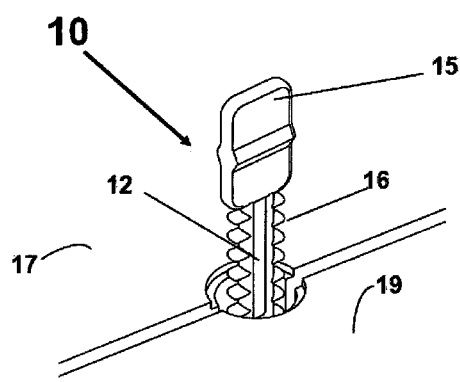
FIG. 3a shows a view of the device of FIG. 1 in a second step of its use in the craniotomial hole.

The bone operculum 19 is repositioned as shown in FIG. 3*a*. In this way, the cortical riser 12 will project from the craniotomial hole.

Figure 4A:
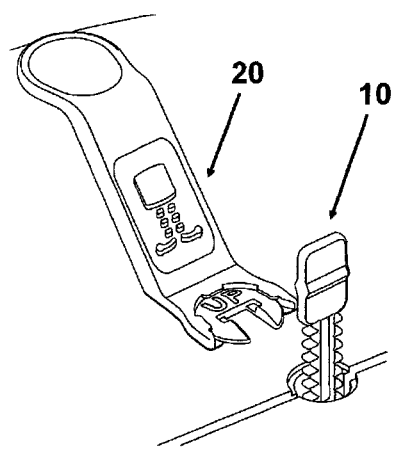
FIG. 4a shows a view of the device of FIG. 1 in a third step of its use in the craniotomial hole, and a preferred embodiment of the applying accessory device in its use.
Figure 6A:
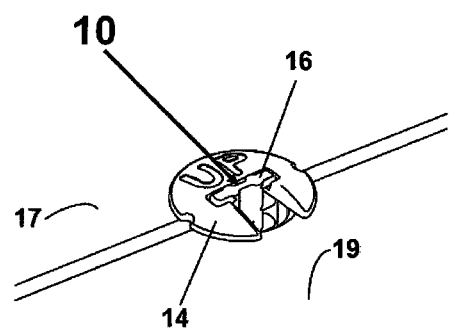
FIG. 6a shows a view of the device of FIG. 1 in the final step of its use in the craniotomial hole.

Afterwards, the surgeon verifies the correct position of the operculum 19, and stretches, by means of the handle 15, the cortical riser 12 and the elastic arms 11 in order to be able to insert the upper plate 14 next to one of the fastening levels 16, like in FIG. 5*a*. When inserting the upper plate 14, the surgeon uses the applying device 20 shown in FIG. 4*a*. In this way, the craniotomial hole will be closed. Finally, the surgeon removes the handle 15 with a cutting device (FIG. 6*a*).

In order to position the device 10 into the craniotomial cutting, the following operations are provided.

A surgeon inserts the device 10 into the craniotomial cutting so that an end of the small transverse arms 13 is placed in the space between the cranial crown 17 and the dura mater 18, with the elastic arms 11 aligned along the direction of the craniotomial cutting and the cortical riser 12 perpendicular to the cranial surface.

Figure 3B:
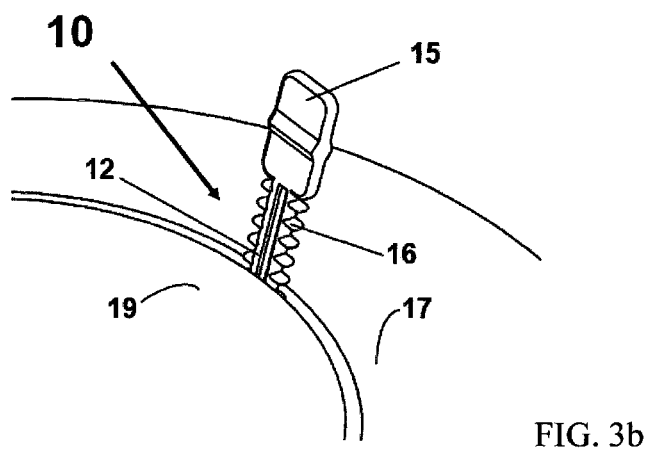
FIG. 3b shows a view of the device of FIG. 1 in a second step of its use in the craniotomial cutting.

The bone operculum 19 is rested onto the other ends of the small transverse arms 13, as shown in FIG. 3*b*. In this way, the riser 12 will project between the cranial crown 17 and the operculum 19.

Figure 4B:
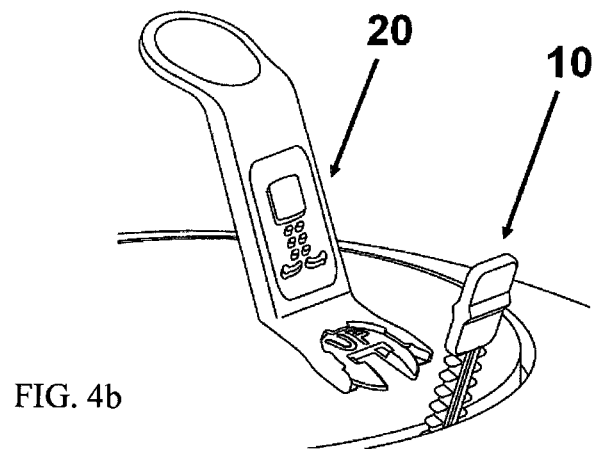
FIG. 4b shows a view of the device of FIG. 1 in a third step of its use in the craniotomial cutting, and a preferred embodiment of the applying accessory device in its use.
Figure 6B:
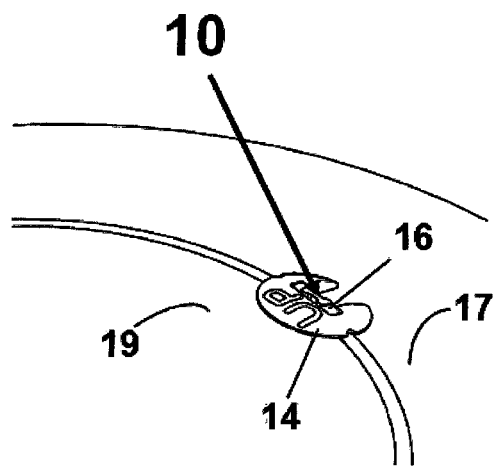
FIG. 6b shows a view of the device of FIG. 1 in the final step of its use in the craniotomial cutting.

Afterwards, the surgeon verifies the correct position of the operculum 19, and stretches, by means of the handle 15, the cortical riser 12 and the elastic arms 11 to be able to insert the upper plate 14 next to one of the fastening levels 16, like in FIG. 5*b*. When inserting the upper plate 14, the surgeon uses the applying device 20 shown in FIG. 4*b*. Finally, the surgeon removes the handle 15 with a cutting device (FIG. 6*b*).

The cranial fastening device 10 of the invention is suitable for all craniotomy cases, since its shape and its suitability to the bone thickness allow keeping the bone limb tended to the cranial crown edge, both on the internal and on the external margin, in order to allow the correct ossification.

At the same time, the elasticity of the bio-compatible plastic material being used guarantees a lower tension on the brain after an operation, namely when brain edema conditions could occur and therefore a swelling of the brain itself.

From the above description, the features are clear for the device 10 for fastening a cranial limb to the cranial crown to be positioned into the craniotomial hole or the craniotomial cutting, object of the present invention, and its advantages are also clear.

Moreover, in the practice of the invention, materials, shapes, sizes of the shown details could be changed according to needs and they could be replaced by other technically equivalent arrangements.

Finally, it is clear that numerous variations could be made to the device 10 for fastening a cranial limb to the cranial crown to be positioned into the craniotomial hole or the craniotomial cutting, object of the present invention, without thereby departing from the scope of the present invention, as defined by the enclosed claims.

The invention claimed is:

1. A device for fastening a cranial limb to a cranial crown adapted to be positioned into a craniotomial cutting, the device comprising:
    a) at least one cortical supporting riser;
    b) a first closing means operatively connected to the cortical riser;
    c) a second closing means adapted to be fastened to the cortical riser to complete closing; and
    d) at least one handle removably connected to the cortical riser and adapted to drive the device to take it from a rest position to an operating fastening position;
    wherein the first closing means comprises at least two elastic arms operatively connected to the cortical riser and wherein each of the elastic arms comprises an ending with at least one small transverse arm forming a T.

2. The device of claim 1, wherein the device comprises elastic material made of biocompatible plastic.

3. The device of claim 1, wherein the second closing means is composed of an upper plate adapted to be inserted into an upper part of the cortical riser.

4. The device of claim 3, wherein the cortical riser further comprises a plurality of fastening elements placed at one or more levels along a length of the riser, wherein the plurality of fastening elements are adapted to engage the upper plate coupling with the riser.

5. The device of claim 4, further comprising an applying device, wherein the applying device comprises a seat adapted to support the second closing means and to provide an operating coupling between the second closing means and the cortical riser when a craniotomial hole, the craniotomial cutting or both the craniotomial hole and the craniotomial cutting has been closed.

6. The device of claim 1, further comprising an applying device, wherein the applying device comprises a seat adapted to support the second closing means and to provide an operating coupling between the second closing means and the cortical riser when a craniotomial hole, the craniotomial cutting or both the craniotomial hole and the craniotomial cutting has been closed.

7. A method for using a device for fastening a cranial limb to a cranial crown when there is a craniotomial hole, comprising the steps of:
    a) providing the device of claim 1;
    b) providing the applying device of claim 6;
    c) inserting the device into a craniotomial hole with the cortical riser placed at a hole centre and perpendicular to a cranial surface, and so that part of the small transverse arms are placed in a space between a cranial crown and dura mater;
    d) repositioning a bone operculum so that the cortical riser projects from the craniotomial hole;
    e) verifying a correct position of the bone operculum and stretching, by means of the handle, the cortical riser and the elastic arms to be able to insert the second closing means next to one of fastening elements;
    f) inserting the second closing means, via the applying device, so that the craniotomial hole is closed; and
    g) removing the handle via cutting means.

8. A method for using a device for fastening a cranial limb to a cranial crown when there is a craniotornial hole, comprising the steps of:
 a) providing the device of claim 1;
 b) providing the applying device of claim 5;
 c) inserting the device into a craniotomial hole with the cortical riser placed at a hole centre and perpendicular to a cranial surface, and so that part of the small transverse arms are placed in a space between a cranial crown and dura mater;
 d) repositioning a bone operculum so that the cortical riser projects from the craniotomial hole;
 e) verifying the correct position of the operculum and stretching, by means of the handle, the cortical riser and the elastic arms to be able to insert the second closing means next to one of the fastening elements;
 f) inserting the second closing means, via the applying device, so that the craniotomial hole is closed; and
 g) removing the handle via cutting means.

9. A method for using a device for fastening a cranial limb to a cranial crown when there is a craniotomial hole, the method comprising the steps of:
 a) providing the device of claim 4;
 b) providing the applying device of claim 5;
 c) inserting the device into the craniotomial hole with the cortical riser placed at a hole centre and perpendicular to a cranial surface, and so that part of the small transverse arms are placed in a space between a cranial crown and dura mater;
 d) repositioning a bone operculum so that the cortical riser projects from the craniotomial hole;
 e) verifying a correct position of the operculum and stretching, by means of the handle, the cortical riser and the elastic arms to be able to insert the second closing means next to one of the fastening elements;
 f) inserting the second closing means, through the applying device, so that the craniotomial hole is closed; and
 g) removing the handle through cutting means.

* * * * *